(12) United States Patent
Altmann et al.

(10) Patent No.: US 7,723,020 B2
(45) Date of Patent: *May 25, 2010

(54) USE OF AZETIDINONE COMPOUNDS

(75) Inventors: Scott W. Altmann, Fanwood, NJ (US); Duane A. Burnett, Bernardsville, NJ (US); Harry R. Davis, Jr., Berkeley Heights, NJ (US); Michael P. Graziano, Scotch Plains, NJ (US); Maureen Laverty, Old Bridge, NJ (US); Xiaorui Yao, Piscataway, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/586,303

(22) Filed: Oct. 25, 2006

(65) Prior Publication Data

US 2007/0105141 A1    May 10, 2007

Related U.S. Application Data

(60) Continuation of application No. 11/123,615, filed on May 6, 2005, now Pat. No. 7,144,696, which is a division of application No. 10/438,637, filed on May 15, 2003, now Pat. No. 6,933,107, which is a division of application No. 09/547,509, filed on Apr. 12, 2000, now Pat. No. 6,593,078.

(60) Provisional application No. 60/129,610, filed on Apr. 16, 1999.

(51) Int. Cl.
    C12Q 1/00    (2006.01)
    G01N 33/53   (2006.01)
    G01N 33/567  (2006.01)
    A01N 43/04   (2006.01)
    A61K 31/397  (2006.01)

(52) U.S. Cl. .................. 435/4; 435/7.1; 435/7.2; 435/7.21; 514/23; 514/210.02

(58) Field of Classification Search .............. 435/4, 435/7.1, 7.2; 514/23, 210.02
See application file for complete search history.

(56) References Cited

U.S. PATENT DOCUMENTS

| 4,144,232 | A |   | 3/1979  | Koppel et al. |
| 4,375,475 | A |   | 3/1983  | Willard et al. |
| 4,443,372 | A |   | 4/1984  | Luo et al. |
| 4,479,900 | A |   | 10/1984 | Luo et al. |
| 4,500,456 | A |   | 2/1985  | Spitzer et al. |
| 4,576,749 | A |   | 3/1986  | Zahler et al. |
| 4,576,753 | A |   | 3/1986  | Kamiya et al. |
| 4,595,532 | A |   | 6/1986  | Miller |
| 4,620,867 | A |   | 11/1986 | Luo |
| 4,633,017 | A |   | 12/1986 | Mueller et al. |
| 4,675,399 | A |   | 6/1987  | Miller |
| 4,680,391 | A |   | 7/1987  | Firestone et al. |
| 4,784,734 | A |   | 11/1988 | Torii et al. |
| 4,794,108 | A |   | 12/1988 | Kishimoto et al. |
| 4,803,266 | A |   | 2/1989  | Kawashima et al. |
| 4,834,846 | A |   | 5/1989  | Abramson et al. |
| 4,876,365 | A |   | 10/1989 | Kirkup et al. |
| 4,879,069 | A |   | 11/1989 | Morand et al. |
| 4,983,597 | A |   | 1/1991  | Yang et al. |
| 5,030,628 | A |   | 7/1991  | Joyeau et al. |
| 5,099,034 | A |   | 3/1992  | Yoshida et al. |
| 5,120,729 | A |   | 6/1992  | Chabala et al. |
| 5,229,381 | A |   | 7/1993  | Doherty et al. |
| 5,229,510 | A |   | 7/1993  | Knight et al. |
| 5,266,490 | A | * | 11/1993 | Davis et al. ............ 435/320.1 |
| 5,306,817 | A |   | 4/1994  | Thiruvengadam et al. |
| 5,348,953 | A |   | 9/1994  | Doherty et al. |
| 5,350,868 | A |   | 9/1994  | Yoshida et al. |
| 5,412,092 | A |   | 5/1995  | Rey et al. |
| 5,550,229 | A |   | 8/1996  | Iwasaki et al. |
| 5,602,003 | A | * | 2/1997  | Pierce et al. ............ 435/69.1 |
| 5,661,145 | A |   | 8/1997  | Davis |
| 5,688,785 | A |   | 11/1997 | Vaccaro |
| 5,688,787 | A |   | 11/1997 | Burnett et al. |
| 5,688,990 | A |   | 11/1997 | Shankar |
| 5,728,827 | A |   | 3/1998  | Thiruvengadam et al. |
| 5,817,806 | A |   | 10/1998 | Rossi et al. |
| 5,847,115 | A |   | 12/1998 | Iwasaki et al. |
| 5,925,333 | A |   | 7/1999  | Krieger et al. |
| 6,031,094 | A |   | 2/2000  | Tsien et al. |

FOREIGN PATENT DOCUMENTS

| DE | 2046823 | 3/1972 |
| EP | 0199630 | 10/1986 |
| EP | 0219876 | 4/1987 |

(Continued)

OTHER PUBLICATIONS

Ram et al., 1990, Indian J. Chem., Sect B. 29B 12:1134-7.

(Continued)

*Primary Examiner*—Sue Liu

(57) ABSTRACT

The use of azetidinone compounds that are inhibitors of cholesterol absorption as tools for discovering and characterizing proteins involved in trafficking or absorption of cholesterol and/or cholesteryl esters in biological systems is presented. These compounds can serve as tools for competitive binding assays to discover and characterize other chemical agents useful as cholesterol absorption inhibitors. New compounds of the present invention are also highly efficacious inhibitors of cholesterol absorption.

6 Claims, No Drawings

FOREIGN PATENT DOCUMENTS

| | | |
|---|---|---|
| EP | 0264231 | 4/1988 |
| EP | 0267878 | 5/1988 |
| EP | 0323807 | 7/1989 |
| EP | 0333268 | 9/1989 |
| EP | 0337549 | 10/1989 |
| EP | 0365364 | 4/1990 |
| EP | 0390112 | 10/1990 |
| EP | 0415487 | 3/1991 |
| EP | 0462667 | 12/1991 |
| EP | 0 481 671 A1 | 4/1992 |
| EP | 0524595 | 1/1993 |
| GB | 2203149 | 10/1988 |
| WO | WO 87/04429 | 7/1987 |
| WO | WO93/02048 | 2/1993 |
| WO | WO94/17038 | 8/1994 |
| WO | WO95/01356 | 1/1995 |
| WO | WO97/18304 | 5/1997 |

OTHER PUBLICATIONS

Hoekman et al., 1982, J. Agric. Food Chem., 30:920-924.
Durst et al., 1972, Can. J. Chem., 50:3196-3201.
Otto et al., 1983, Liebigs Ann. Chem., pp. 1152-1161.
Panfil, et al., 1986, Heterocycles 24:6 pp. 1609-17.
Schnitzer-Polokoff et al., 1991, Comp. Biochem. Physiol., 99A: pp. 665-670.
Witzum, Circulation, 1989, 80:5 pp. 1101-1114.
Illingworth, Drugs 1988, 36:Supp.3 pp. 63-71.
Allain et al., Clin. Chem., 1974, 20:470-475.
Horie et al., Atherosclerosis, 1991, 88:183-192.
Baxter et al., J. Biological Chem., 1992, 276:17 pp. 11705-11708.
Salisbury, Atherosclerosis 1995, 115:45-63.
Burrier, Biochemical Pharmacology, 1994, 47:9 pp. 1545-1551.
Harwood, H. James, Jr. et al., Journal of Lipid Research, 1993, 34:377-395.
Current Drugs: Anti-Atherosclerotic Agents—Summary Factfile, May 1992.
Bruns, Robert F., et al., "Characterization of the $A_2$ Adenosine Receptor Labeled by [$^3$H]NECA in Rat Striatal Membranes"; Molelcular Pharmacology, 29:331-346 (1986).
Collis, M.G., "Evidence for an $A_1$-adenosine receptor in the guinea-pig atrium"; Br. J. Pharmac, 78:207-212 (1983).
Jarvis, Michael F., et al., "[$^3$H]CGS 21680, A Selective $A_2$ Adenosine Receptor Agonist Directly Labels $A_2$ Receptors in Rat Brain"; The Journal of Pharmacology and Experimental Therapeutics; 251(3):888-893 (1989).
Stone, Trevor W., "Purine Receptors and their Pharmacological Roles,"; Advances in Drug Research, 18:291-429 (1989).
Georg, Gunda I. et al., Tetrahedron Letters, 1985, 26:33 pp. 3903-3906.
Hart, David J., et al., Tetrahedron Letters, 1985, 26:45 pp. 5493-5496.
Simova, E. , The American Chemical Society, Chemical Abstracts, 1977, 86:15 1-556.
Otto et al., The American Chemical Society, Chemical Abstracts, 1983, 99:19 1-661.
Nobuki, O. et al., The American Chemical Society, Chemical Abstract, 1977, 106:17 1-727.
Mayrhofer, Roswitha, et al., 1980. Communications, pp. 247-248.
Burrier, et al., 1994, The Journal of Pharmacology and Experimental Therapeutics, 272:1 pp. 156-163.
Clader, John W., et al., 1995. Journal of Medicinal Chemistry, 38:10 pp. 1600-1607.
Sybertz, Edmunh J., et al., 1995, Atherosclerosis, pp. 311-315.
Olsson, R.A., Physiological Reviews. 70:3 Jul. 1990, pp. 761-845.
Daly, John W., Journal of Medicinal Chemistry, 25:3 Mar. 1982, pp. 197-207.
Belardinelli, Luiz, et al., 1989, Progress in Cardiovascular Diseases, 32:1 pp. 73-97.
Jacobson, Kenneth A., et al., 1992, Journal of Medicinal Chemistry, 35:3 pp. 4143-4149.
Conti, A. et al., "Role of 5-HT2 Receptors in Serotonin-Induced Contraction in the Human Mammary Artery," European Journal of Pharmacology. 1990, 176:207-212.
Born, G.V.R. et al., "The Aggregation of Blood Platelets," J. Physiol., 1963, 168:178-195.
Monopoli, A. et al., "Antihypertensive Activity of a New ACE-Inhibitor, SCH 33844, during Repeated Administration in Spontaneously Hypertensive Rats," 1987, Arch. Int. Pharmacodyn 286:246-254.
Cristalli, Gloria et al., J. Med. Chem., 1992, 35:2363-2368.
Bruns, Robert F., et al., 1980, Proc. Natl. Acad. Sci. 77:9 pp. 5547-5551.
Mukherjuee, S. et al., Biophysical Journal, 75:1915 (XP000938151) ISSN: 0006-3495 abstract (Oct. 1998).
Vaccaro, W. D. et al., Bioorganic & Medicinal Chemistry Letters, 8:313-318 (XP004136870) ISSN: 0960-894X (Feb. 3, 1998).
Acton et al., The Journal of Biological Chemistry, 269:33 pp. 21003-21009 (Aug. 19, 1994).
Schroeder, F. et al., "Cholesterol Domains in Biological Membranes", Mol. Membr. Biol., 12:113 (XP000938276) abstract (1995).
Hesk, D. et al., "Synthesis of $^3$H and $^{14}$C Labelled Sch 48461", Journal of Labelled Compounds and Radiopharmaceuticals, 38:1039 (XP000938019) ISSN: 0362-4803 (1996).
Stone, Trevor W. Purine receptors and their pharmacological roles. Advance in Drug Research 18: 291-429 (1989).
Collis MG. Evidence for an A1-adenosine receptor in the guinea-pig atrium. Br J Pharmacol. Jan. 1983;78(1):207-12.
Jarvis MF, Schultz R, Hutchison AJ, Do UH, Sills MA, Williams M. [$^3$H]CGS 21680, a selective A2 adenosine receptor agonist directly labels A2 receptors in rat brain. J Pharmacol Exp Ther. Dec. 1989;251(3):888-93.
Bruns RF, Lu GH, Pugsley TA. Characterization of the A2 adenosine receptor labeled by [$^3$H]NECA in rat striatal membranes. Mol Pharmacol. Apr. 1986;29(4):331-46.

\* cited by examiner

USE OF AZETIDINONE COMPOUNDS

This application is a continuation of U.S. application Ser. No. 11/1123,615, filed May 6, 2005, now U.S. Pat. No. 7,144,696, which is a divisional of U.S. application Ser. No. 10/438,637, filed May 15, 2003, now U.S. Pat. No. 6,933,107, which is a divisional of U.S. application Ser. No. 09/547,509, filed Apr. 12, 2000, now U.S. Pat. No. 6,593,078, which claims priority under 35 U.S.C. §119(e) to U.S. Application Ser. No. 60/129,610, filed Apr. 16, 1999, now abandoned, each of which are herein incorporated by reference in their entireties.

FIELD OF THE INVENTION

The present invention relates to the use of azetidinone compounds that are inhibitors of cholesterol absorption as tools for discovering and characterizing proteins involved in trafficking or absorption of cholesterol and/or cholesteryl esters in biological systems. Further, these compounds can serve as tools for competitive binding assays to discover and characterize other chemical agents useful as cholesterol absorption inhibitors. New compounds of the present invention are highly efficacious inhibitors of cholesterol absorption.

BACKGROUND OF THE INVENTION

Atherosclerotic coronary heart disease (CHD) represents the major cause for death and cardiovascular morbidity in the western world. Risk factors for CHD include hypertension, diabetes mellitus, family history, male gender, cigarette smoke and serum cholesterol. A total cholesterol level in excess of 225 to 250 mg/dl is associated with significant elevation of risk of CHD.

Cholesteryl esters are a major component of atherosclerotic lesions and the major storage form of cholesterol in arterial wall cells. Formation of cholesteryl esters is also a key step in the intestinal absorption of dietary cholesterol. Thus, inhibition of cholesteryl ester formation and reduction of serum cholesterol is likely to inhibit the progression of atherosclerotic lesion formation, decrease the accumulation of cholesteryl esters in the arterial wall, and block the intestinal absorption of dietary cholesterol.

The regulation of whole-body cholesterol homeostasis in humans and animals involves the regulation of dietary cholesterol and modulation of cholesterol biosynthesis, bile acid biosynthesis and the catabolism of the cholesterol-containing plasma lipoproteins. The liver is the major organ responsible for cholesterol biosynthesis and catabolism and for this reason, it is a prime determinant of plasma cholesterol levels. The liver is the site of synthesis and secretion of very low density lipoproteins (VLDL) which are subsequently metabolized to low density lipoproteins (LDL) in the circulation. LDL are the predominant cholesterol-carrying lipoproteins in the plasma and an increase in their concentration is correlated with increased atherosclerosis.

When intestinal cholesterol absorption is reduced, by whatever means, less cholesterol is delivered to the liver. The consequence of this action is decreased hepatic lipoprotein production, and an increase in the hepatic clearance of plasma cholesterol, mostly as LDL. Thus, the net effect of inhibiting intestinal cholesterol absorption is a decrease in plasma cholesterol levels.

Certain azetidinone core structures have been reported to be useful in lowering cholesterol levels by decreasing intestinal cholesterol absorption. These related azetidinone cores and their synthesis are detailed in the following commonly assigned U.S. patents, the disclosures of which are incorporated, in their entirety, herein by reference: U.S. Pat. Nos. 5,688,787; 5,698,548; 5,624,920; 5,631,365; 5,633,246; 5,656,624; 5,744,467; and 5,767,115. The discovery of 2-azetidinones as potent and selective intestinal cholesterol absorption inhibitors has confirmed this mechanism as a key point of intervention for lowering cholesterol plasma levels and has validated the therapeutic value of such an approach.

The mechanism by which cholesterol moves from the lumen into the epithelial layer lining the small intestine is not well understood. Recent experimental evidence supports the notion of an active transport process mediated by a protein or proteins in the enterocyte brush border membrane rather than a simple diffusion model. Kinetic analysis and sterol specificity of cholesterol uptake as well as the structure-activity relationship studies of the cholesterol absorption inhibitors are consistent with a specific protein receptor/transporter regulated event. Potential molecules for this process have been proposed in recent years. However, the specific biochemical pathway responsible for cholesterol absorption remains to be defined.

Compounds I and II (especially II)

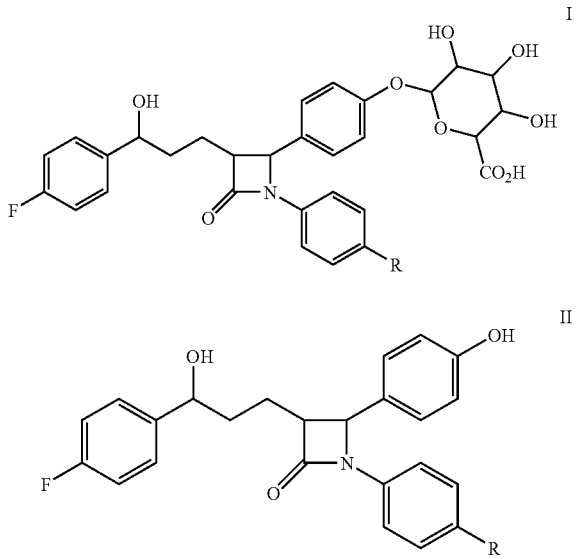

where R is fluorine, are potent inhibitors of cholesterol uptake in animal models and humans. The mechanism by which these compounds and related 2-azetidinones inhibit the uptake of cholesterol across the intestinal wall is not known. These compounds do not sequester bile acids or precipitate cholesterol Nor do they potently inhibit HMG-CoA reductase, pancreatic lipase, or acyl-CoA cholesterol acyl transferase (ACAT). Understanding the mechanism by which these compounds inhibit cholesterol absorption will shed light on the biochemical pathways involved in the uptake of dietary and biliary cholesterol.

SUMMARY OF THE INVENTION

In one aspect, this invention provides a method for identifying a protein involved in cholesterol absorption in a biological system, the method comprising the steps of: (a) providing a cDNA expression library capable of expressing a protein involved in cholesterol absorption in a biological system, said cDNA expression library comprising a plurality of cells capable of expressing different cDNAs; (b) screening said expression library by incubating cells from said library with a fluorescent cholesterol absorption inhibitor; (c) after step (b), identifying the cell or cells in said library that display the greatest amount of fluorescence; and (d) identifying the protein associated with the cDNA expressed by said cell or cells displaying the greatest amount of fluorescence.

In another aspect, this invention provides a method for assaying inhibitory agents for activity against cholesterol absorption, the method comprising the steps of: providing a cell capable of binding a fluorescent cholesterol absorption inhibitor; contacting said cell with a candidate inhibitory agent in the presence of said fluorescent cholesterol absorption inhibitor; and measuring the inhibition of the fluorescence of said cell.

In still another aspect, this invention provides a method for identifying inhibitory agents which inhibit the absorption of cholesterol into a cell membrane, said method comprising the steps of: (a) combining a fluorescent cholesterol absorption inhibitor, said cell membrane and a candidate inhibitory agent, under conditions wherein, but for the presence of said inhibitory agent, said fluorescent cholesterol absorption inhibitor is bound to the membrane; and (b) detecting the relative presence or absence of fluorescent cholesterol absorption inhibitor absorption bound to the membrane, wherein a relative absence of fluorescent cholesterol absorption inhibitor absorption indicates that said candidate inhibitory agent is an inhibitory agent which inhibits cholesterol absorption into the membrane.

In another aspect, this invention provides a method for identifying inhibitory agents which inhibit the absorption of cholesterol, said method comprising the steps oft (a) combining a labeled cholesterol absorption inhibitor, a cell expressing the scavenger receptor type B, class I (SR-SI) and a candidate inhibitory agent, under conditions wherein, but for the presence of said inhibitory agent, said labeled cholesterol absorption inhibitor binds to SR-BI; and (b) detecting the relative presence or absence of labeled cholesterol absorption inhibitor absorption bound to SR-BI wherein a relative absence of labeled cholesterol absorption inhibitor absorption indicates that said candidate inhibitory agent is an inhibitory agent which inhibits SR-BI-mediated cellular cholesterol absorption.

In further aspects, this invention provides proteins and new inhibitory agents identified by the above methods. This invention also provides novel fluorescent cholesterol absorption inhibitors of formulas I and II:

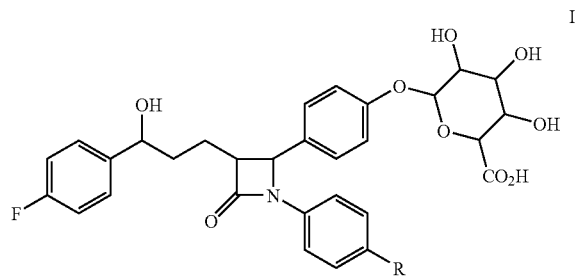

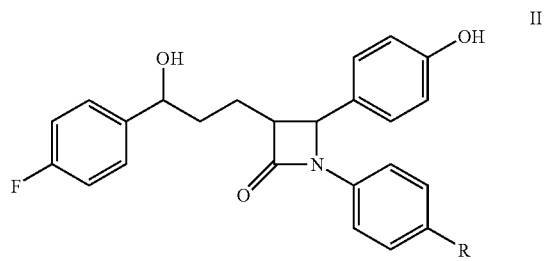

wherein R comprises a fluorescent moiety.

DETAILED DESCRIPTION OF THE INVENTION

A. Novel Fluorescent Cholesterol Absorption Inhibitors

Novel fluorescent cholesterol absorption inhibitors of this invention include compounds of formulas I and II:

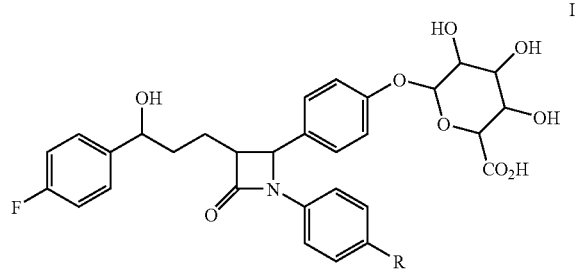

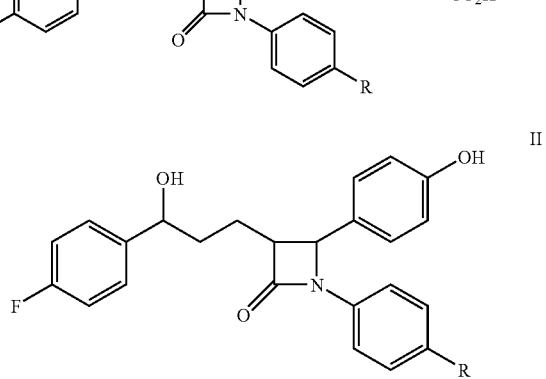

wherein R comprises a fluorescent moiety. In preferred embodiments, R is a fluorescent moiety linked by an alkynyl-containing tether group. In a particularly preferred embodiment, R is selected from the group consisting of:

A.

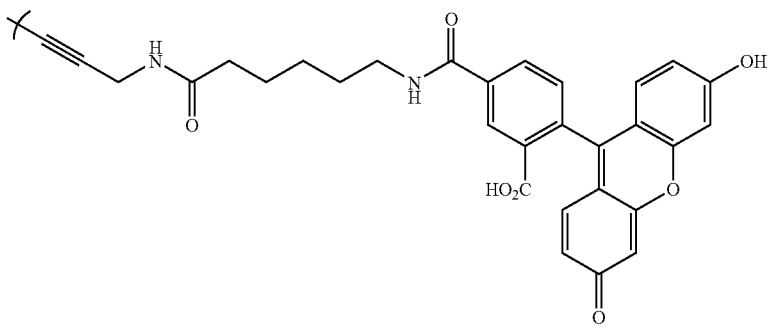

B.

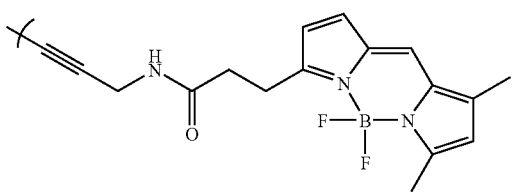

Modification with fluorescent moieties A-B of the N-aryl ring of other azetidinone cholesterol absorption inhibitor core structures related to the above are contemplated as being within the scope of this invention as well. These related azetidinone cores and their synthesis are detailed in the following commonly assigned U.S. patents the disclosures of which are incorporated, in their entirety, herein by reference: U.S. Pat. Nos. 5,688,787; 5,698,548; 5,624,920; 5,631,365; 5,633,246; 5,656,624; 5,744,467; and 5,767,115.

Compounds in the following text are designated as:

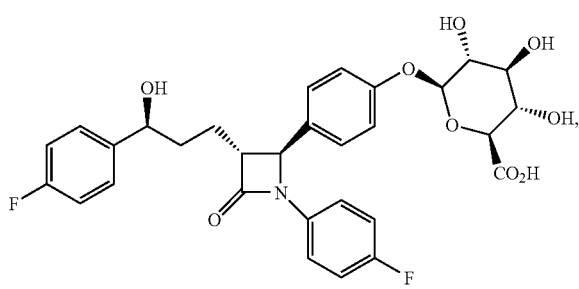

IA

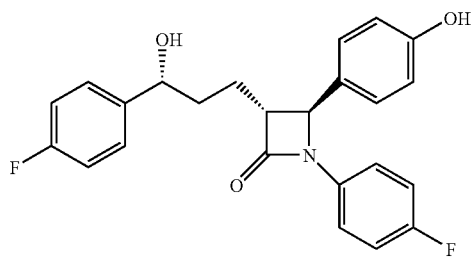

IIA

IIIA
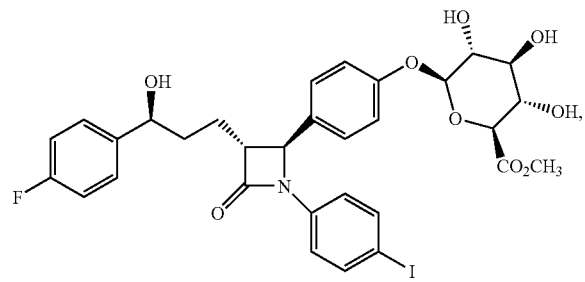
IVA
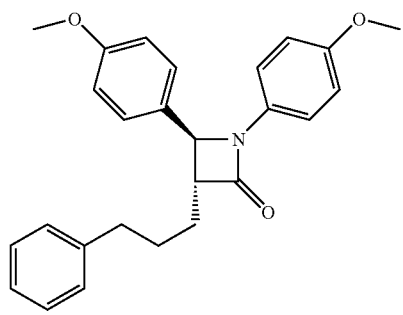
IB
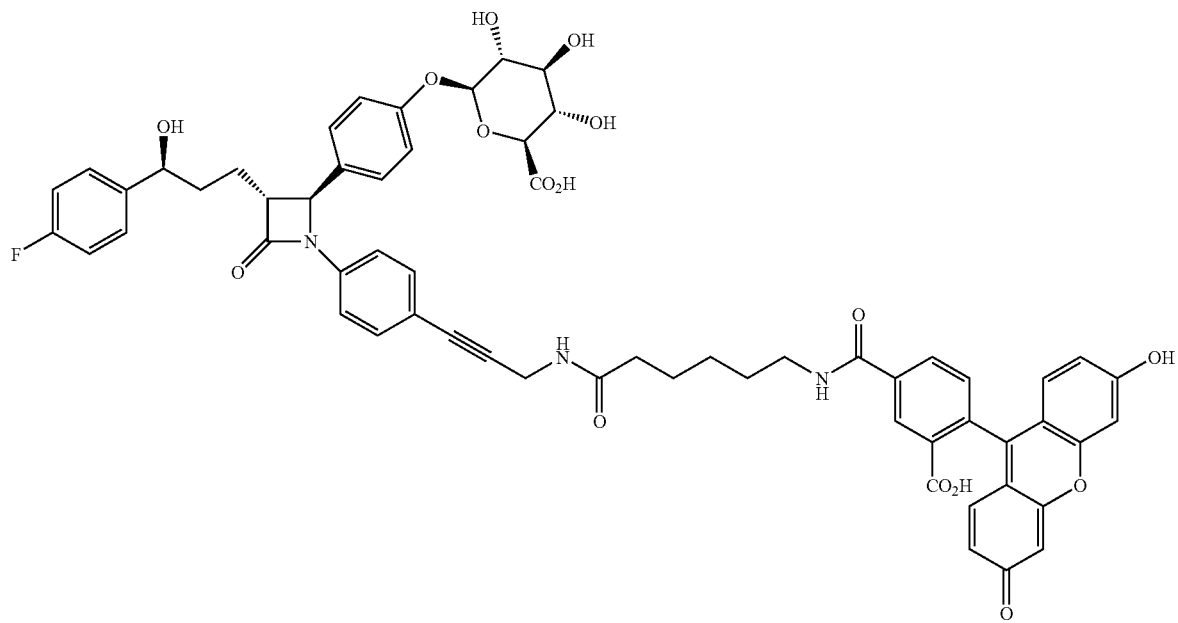

-continued

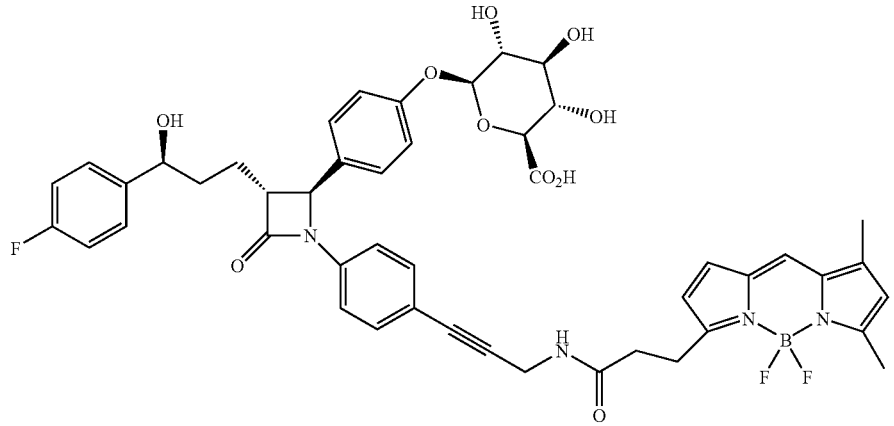

IC

The synthetic route to these fluorescent azetidinones is shown in Scheme 1. The fluorescent alkynyl compounds are prepared from commercially available electrophilic fluorescent derivatives (see Handbook of Fluorescent Probes and Research Chemicals, Molecular Probes, Inc.) and propargyl amine. The syntheses of N-iodophenyl azetidinone derivatives have been described in previous patents, cited above. The fluorescent alkynylated material is then coupled to the N-iodophenylazetidinone via a palladium mediated coupling reaction Deprotection of the glucuronide ester is accomplished as a final step in analogs bearing this moiety.

Scheme 1.

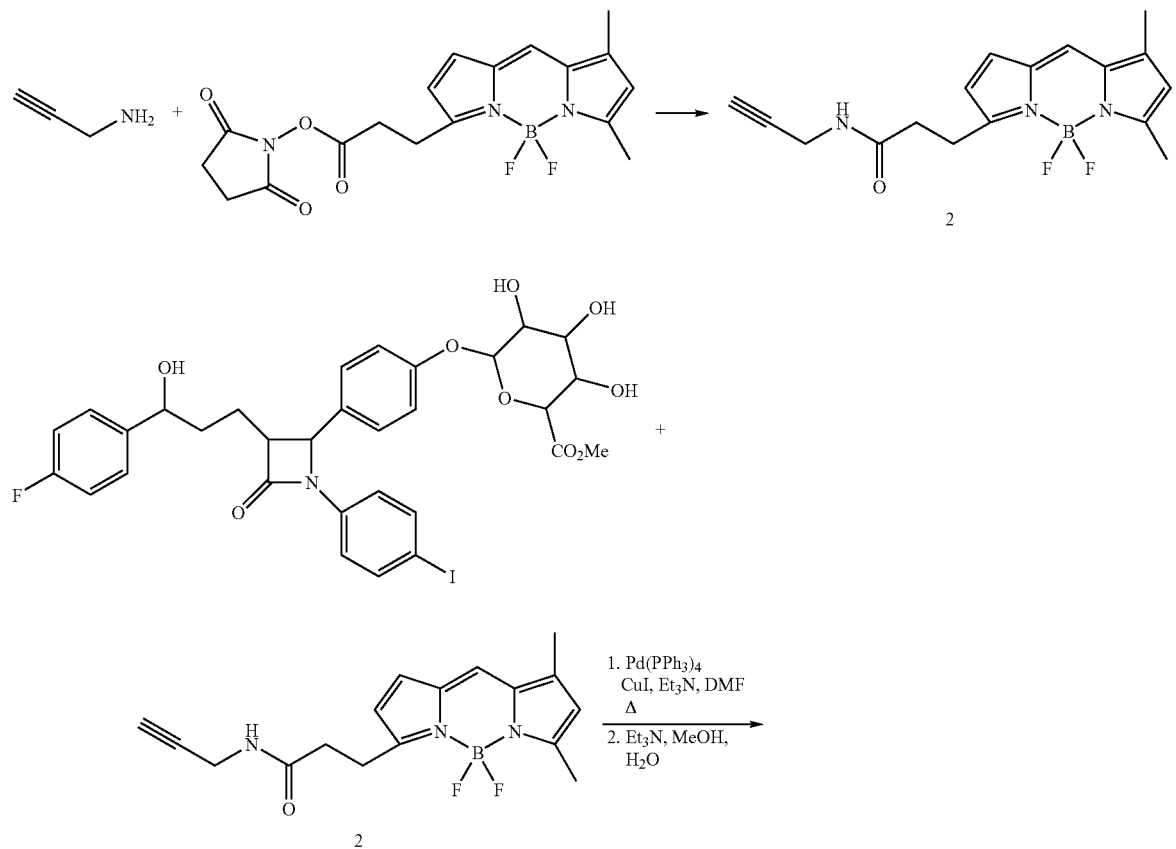

-continued

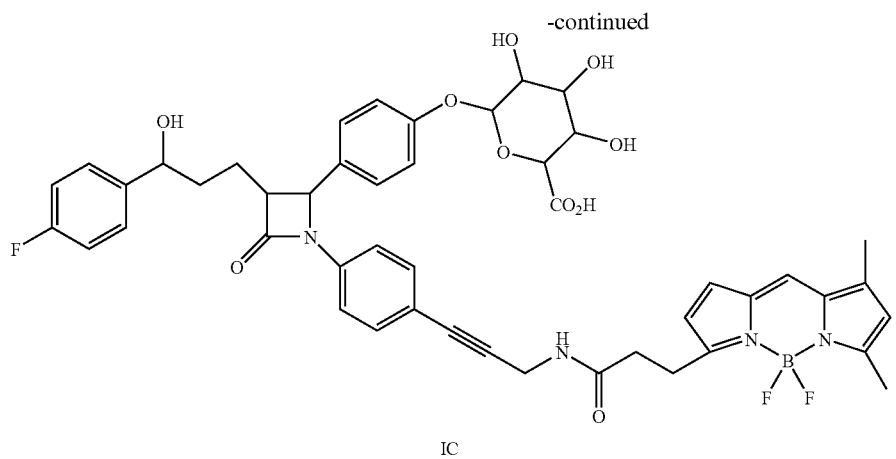

IC

B. General Methods

The practice of the present invention generally employs conventional techniques of molecular biology, microbiology, recombinant DNA, and immunology, which are within the skill of the art. Such techniques are explained fully in the literature. See for example J. Sambrook et al, "Molecular Cloning; A Laboratory Manual (1989); "DNA Cloning" Vol. I and II (D. N. Clover ed. 1985); "Oligonucleotide Synthesis" (M. J. Gait ed, 1984); "Nucleic Acid Hybridization" (S. D. Hames & S. J. Higgins eds. 1984); "Transcription And Translation" (B. D. Hames & S. J. Higgins eds. 1984); "Animal Cell Culture" (R. I. Freshney ed. 1986); "Immobilized Cells And Enzymes" (IRL Press, 1986); B. Perbal, "A Practical Guide To Molecular Cloning" (1984); the series, "Methods In Enzymology" (Academic Press, Inc.); "Gene Transfer Vectors For Mammalian Cells" (J. H. Miller and M. P. Calos eds. 1987, Cold Spring Harbor Laboratory); Meth Enzymol (1987) 154 and 155 (Wu and Grossman, and Wu, eds., respectively); Mayer & Walker, eds. (1987), "Immunochemical Methods In Cell And Molecular Biology" (Academic Press, London); Scopes, "Protein Purification: Principles And Practice", 2nd Ed (Springer-Verlag, N.Y., 1987), and "Handbook Of Experimental Immunology", volumes I-IV (Weir and Blackwell, eds, 1986).

C. Methods of Screening cDNA Libraries cDNA libraries containing genes capable of expressing a protein involved in cholesterol absorption are prepared by standard techniques, such as described in the above references. Both prokaryotic and eukaryotic host cells are useful for expressing desired coding sequences when appropriate control sequences compatible with the designated host are used. Among prokaryotic hosts, *E. coli* is most frequently used. Expression control sequences for prokaryotes include promoters, optionally containing operator portions, and ribosome binding sites. Transfer vectors compatible with prokaryotic hosts are commonly derived from, for example, pBR322, a plasmid containing operators conferring ampicillin and tetracycline resistance, and the various pUC vectors, which also contain sequences conferring antibiotic resistance markers. These plasmids are commercially available. The markers may be used to obtain successful transformants by selection. Commonly used prokaryotic control sequences include the β-lactamase (penicillinase) and lactose promoter systems (Chang et al, Nature (1977) 198:1056), the tryptophan (trp) promoter system (Goeddel et al, Nuc Acids Res (1980) 8:4057) and the lambda-derived $P_L$ promoter and N gene ribosome binding site (Shimatake et al, Nature (1981) 292:128) and the hybrid tac promoter (De Boer et al, Proc Nat Acad Sci USA (1983) 292:128) derived from sequences of the trp and lac UV5 promoters. The foregoing systems are particularly compatible with *E. coli*; if desired, other prokaryotic hosts such as strains of *Bacillus* or *Pseudomonas* may be used, with corresponding control sequences.

Eukaryotic hosts include without limitation yeast and mammalian cells in culture systems. Yeast expression hosts include *Saccharomyces, Klebsiella, Picia,* and the like. *Saccharomyces cerevisiae* and *Saccharomyces carlsbergensis* and *K. lactis* are the most commonly used yeast hosts, and are convenient fungal hosts. Yeast-compatible vectors carry markers which permit selection of successful transformants by conferring prototrophy to auxotrophic mutants or resistance to heavy metals on wild-type strains. Yeast compatible vectors may employ the 2 µ origin of replication (Broach et al, Meth Enzymol (1983) 101:307), the combination of CEN3 and ARS1 or other means for assuring replication, such as sequences which will result in incorporation of an appropriate fragment into the host cell genome. Control sequences for yeast vectors are known in the art and include promoters for the synthesis of glycolytic enzymes (Hess et al, J Adv Enzyme Reg (1968) 7:149; Holland et al, Biochem (1978), 17:4900), including the promoter for 3-phosphoglycerate kinase (R. Hitzeman et al, J Biol Chem (1980) 255:2073). Terminators may also be included, such as those derived from the enolase gene (Holland, J Biol Chem (1981) 256:1385). Particularly useful control systems are those which comprise the glyceraldehyde-3 phosphate dehydrogenase (GAPDH) promoter or alcohol dehydrogenase (ADH) regulatable promoter, terminators also derived from GAPDH, and if secretion is desired, a leader sequence derived from yeast alpha-factor (see U.S. Pat. No. 4,870,008, incorporated herein by reference).

In addition, the transcriptional regulatory region and the transcriptional initiation region which are operably linked may be such that they are not naturally associated in the wild-type organism. These systems are described in detail in EPO 120,551, published Oct. 3, 1984; EPO 116,201, published Aug. 22, 1984; and EPO 164,556, published Dec. 18, 1985, all of which are hereby incorporated herein by reference in full.

Mammalian cell lines available as hosts for expression are known in the art and include many immortalized cell lines available from the American Type Culture Collection (ATCC), including HeLa cells, Chinese hamster ovary (CHO) cells, baby hamster kidney (BHK) cells, and a number of other cell lines. Suitable promoters for mammalian cells are also known in the art and include vital promoters such as that from Simian Virus 40 (SV40) (Fiers et al, Nature (1978) 273:113), Rous sarcoma virus (RSV), adenovirus (ADV), and bovine papilloma virus (BPV). Mammalian cells may also require terminator sequences and poly-A addition sequences. Enhancer sequences which increase expression may also be included, and sequences which promote amplification of the gene may also be desirable (for example methotrexate resistance genes). These sequences are known in the art.

Vectors suitable for replication in mammalian cells are known in the art, and may include vital replicons, or sequences which insure integration of the appropriate sequences into the host genome. For example, another vector used to express foreign DNA is Vaccinia virus. In this case the heterologous DNA is inserted into the Vaccinia genome. Techniques for the insertion of foreign DNA into the vaccinia virus genome are known in the art, and may utilize, for example, homologous recombination. The heterologous DNA is generally inserted into a gene which is non-essential to the virus, for example, the thymidine kinase gene (tk), which also provides a selectable marker. Plasmid vectors that greatly facilitate the construction of recombinant viruses have been described (see, for example, Mackett et al, J Virol (1984) 49:857; Chakrabarti et al, Mol Cell Biol (1985) 5:3403; Moss, in GENE TRANSFER VECTORS FOR MAMMALIAN CELLS (Miller and Calos, eds., Cold Spring Harbor Laboratory, N.Y., 1987), p. 10). Expression of the polypeptide then occurs in cells or animals which are infected with the live recombinant vaccinia virus.

Transformation may be by any known method for introducing polynucleotides into a host cell, including, for example packaging the polynucleotide in a virus and transducing a host cell with the virus, and by direct uptake of the polynucleotide. The transformation procedure used depends upon the host to be transformed. Bacterial transformation by direct uptake generally employs treatment with calcium or rubidium chloride (Cohen, Proc Nat Acad Sci USA (1972) 69:2110; T. Maniatis et at, "Molecular Cloning; A Laboratory Manual" (Cold Spring Harbor Press, Cold Spring Harbor, N.Y., 1982). Yeast transformation by direct uptake may be carried out using the method of Hinnen et al, Proc Nat Acad Sci USA (1978) 75:1929. Mammalian transformations by direct uptake may be conducted using the calcium phosphate precipitation method of Graham and Van der Eb, Virol (1978) 52:546, or the various known modifications thereof. Other methods for introducing recombinant polynucleotides into cells, particularly into mammalian cells, include dextran-mediated transfection, calcium phosphate mediated transfection, polybrene mediated transfection, protoplast fusion, electroporation, encapsulation of the polynucleotide(s) in liposomes, and direct microinjection of the polynucleotides into nuclei.

Vector construction employs techniques which are known in the art, Site-specific DNA cleavage is performed by treating with suitable restriction enzymes under conditions which generally are specified by the manufacturer of these commercially available enzymes. In general, about 1 µg of plasmid or DNA sequence is cleaved by 1 unit of enzyme in about 20 µL buffer solution by incubation for 1-2 hr at 37° C. After incubation with the restriction enzyme, protein is removed by phenol/chloroform extraction and the DNA recovered by precipitation with ethanol. The cleaved fragments may be separated using polyacrylamide or agarose gel electrophoresis techniques, according to the general procedures described in Meth Enzymol (1980) 65:499-560.

Sticky-ended cleavage fragments may be blunt ended using E. coli DNA polymerase I (Klenow fragment) with the appropriate deoxynucleotide triphosphates (dNTPs) present in the mixture. Treatment with S1 nuclease may also be used, resulting in the hydrolysis of any single stranded DNA portions.

Ligations are carried out under standard buffer and temperature conditions using T4 DNA ligase and ATP; sticky end ligations require less ATP and less ligase than blunt end ligations. When vector fragments are used as part of a ligation mixture, the vector fragment is often treated with bacterial alkaline phosphatase (BAP) or calf intestinal alkaline phosphatase to remove the 5'-phosphate, thus preventing religation of the vector. Alternatively, restriction enzyme digestion of unwanted fragments can be used to prevent ligation. Ligation mixtures are transformed into suitable cloning hosts, such as E. coli, and successful transformants selected using the markers incorporated (e.g., antibiotic resistance), and screened for the correct construction.

Synthetic oligonucleotides may be prepared using an automated oligonucleotide synthesizer as described by Warner, DNA (1984) 3:401. If desired, the synthetic strands may be labeled with $^{32}P$ by treatment with polynucleotide kinase in the presence of $^{32}P$-ATP under standard reaction conditions.

For routine vector constructions, ligation mixtures are transformed into E. coli strain HB101 or other suitable hosts, and successful transformants selected by antibiotic resistance or other markers. Plasmids from the transformants are then prepared according to the method of Clewell et al, Proc Nat Acad Sci USA (1969) 62:1159, usually following chloramphenicol amplification (Clewell, J Bacteriol (1972) 110:667). The DNA is isolated and analyzed, usually by restriction enzyme analysis and/or sequencing. Sequencing may be performed by the dideoxy method of Sanger et at, Proc Nat Acad Sci USA (1977) 74:5463, as further described by Messing et at, Nuc Acids Res (1981) 9:309, or by the method of Maxam et at, Meth Enzymol (1980) 65:499. Problems with band compression, which are sometimes observed in GC-rich regions, were overcome by use of T-deazoguanosine according to Barr et al, Biotechniques (1986) 4:428.

Preferably, the cDNA libraries used in this invention are derived from the mRNA of cells or cell lines known to be involved in cholesterol absorption. In a preferred embodiment of this invention, the cDNA library is derived from the mRNA of an intestinal epithelial cell. The cDNA libraries are then screened by incubating cells from the library with a fluorescent cholesterol absorption inhibitor, and identifying those cells that display the greatest amount of fluorescence, using, for example, fluorescence activated cell sorting (FACS). The cDNA expressed in that cell can then be identified using known techniques.

D. Methods of Screening for Inhibitory Agents

New cholesterol absorption inhibitory agents are screened using methods of the invention. In general, a substrate is employed which mimics the protein's natural substrate, but which provides a quantifiable signal when bound. The signal is preferably detectable by colorimetric or fluorometric means: however, other methods such as HPLC or silica gel chromatography, GC-MS, nuclear magnetic resonance, and the like may also be useful. After optimum substrate and protein (or membrane or cell) concentrations are determined, a candidate inhibitory agent is added to the reaction mixture at a range of concentrations. The assay conditions ideally should resemble the conditions under which cholesterol absorption is to be inhibited in vivo, i.e., under physiologic pH, temperature, ionic strength, etc. Suitable inhibitors will exhibit absorption inhibition at concentrations which do not raise toxic side effects in the subject. Inhibitors which compete for binding may require concentrations equal to or greater than the substrate concentration, while inhibitors capable of binding irreversibly to the cholesterol binding site may be added in concentrations on the order of the protein concentration.

This invention provides several methods for assaying, identifying or screening inhibitory agents for activity against cholesterol absorption, including cellular techniques, membrane techniques, and techniques using proteins that are involved in cholesterol absorption, such as the one provided by the current invention, the scavenger receptor type B, class I (SR-BI). SR-BI was first described by Acton et al., *J. Biol. Chem.* (1994) 269:21003-21009. Screening for inhibitory agents is accomplished as described below.

In the cellular method, cells capable of binding a fluorescent cholesterol absorption inhibitor are used. In a preferred embodiment, the cells are involved in cholesterol absorption in a biological system. The cells are contacted with candidate inhibitory agents in the presence of the fluorescent cholesterol absorption inhibitor; the inhibition of the fluorescence of said cells are measured.

In the membrane method, a membrane capable of absorbing cholesterol is used. In a preferred embodiment of this invention, the membranes are from the intestinal brush border. The membranes are contacted with candidate inhibitory agents in the presence of the fluorescent cholesterol absorption inhibitor; and the relative presence or absence of fluorescent cholesterol absorption inhibitor absorption bound to the membrane is measured. A relative absence of fluorescent cholesterol absorption inhibitor absorption indicates that said candidate inhibitory agent is an inhibitory agent which inhibits cholesterol absorption into the membrane.

In the protein method, a cell expressing the scavenger receptor type B, class I (SR-BI) is used. The cell is contacted with a labeled cholesterol absorption inhibitor and a candidate inhibitory agent under conditions wherein, but for the presence of said inhibitory agent, the labeled cholesterol absorption inhibitor binds to SR-BI, and the relative presence or absence of labeled cholesterol absorption inhibitor absorption bound to SR-BI is detected. A relative absence of labeled cholesterol absorption inhibitor absorption indicates that the candidate inhibitory agent is an inhibitory agent which inhibits SR-BI-mediated cellular cholesterol absorption.

The methods of assaying or selecting inhibitory agents of this invention use labeled cholesterol absorption inhibitors. The inhibitors themselves are described in section A, above. The labels used in the assays of invention can be primary labels (where the label comprises an element which is detected directly) or secondary labels (where the detected label binds to a primary label, e.g., as is common in immunological labeling). An introduction to labels, labeling procedures and detection of labels is found in Polak and Van Noorden (1997) Introduction to Immunocytochemistry, second edition, Springer Verlag, N.Y. and in Haugland (1996) Handbook of Fluorescent Probes and Research Chemicals, a combined handbook and catalogue Published by Molecular Probes, Inc., Eugene, Oreg. Primary and secondary labels can include undetected elements as well as detected elements. Useful primary and secondary labels in the present invention can include spectral labels, which include fluorescent labels such as fluorescent dyes (e.g., fluorescein and derivatives such as fluorescein isothiocyanate (FITC) and Oregon Green™, rhodamine and derivatives (e.g., Texas red, tetramethylrhodamine isothiocyanate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$p, etc.), enzymes (e.g., horseradish peroxidase, alkaline phosphatase etc.) spectral colorimetric labels such as colloidal gold or colored glass or plastic (e.g. polystyrene, polypropylene, latex, etc.) beads. The label may be coupled directly or indirectly to the cholesterol absorption inhibitor according to methods well known in the art. As indicated above, a wide variety of labels may be used, with the choice of label depending on sensitivity required, ease of conjugation with the compound, stability requirements, available instrumentation, and disposal provisions. In general, a detector which monitors a protein/inhibitory agent interaction is adapted to the particular label which is used. Typical detectors include spectrophotometers, photomultiplier tubes and photodiodes, microscopes, scintillation counters, cameras, film and the like, as well as combinations thereof. Examples of suitable detectors are widely available from a variety of commercial sources known to persons of skill.

Preferred labels include those which utilize 1) chemiluminescence (using horseradish peroxidase or alkaline phosphatase with substrates that produce photons as breakdown products) with kits being available, e.g., from Molecular Probes, Amersham, Boehringer-Mannheim, and Life Technologies/Gibco BRL; 2) color production (using both horseradish peroxidase or alkaline phosphatase with substrates that produce a colored precipitate) (kits available from Life Technologies/Gibco BRL, and Boehringer-Mannheim); 3) fluorescence (e.g., using Cy-5 (Amersham), fluorescein, and other fluorescent tags); 5) radioactivity. Other methods for labeling and detection will be readily apparent to one skilled in the art.

Fluorescent labels are highly preferred labels, having the advantage of requiring fewer precautions in handling, and being amendable to high-throughput visualization techniques (optical analysis including digitization of the image for analysis in an integrated system comprising a computer). Preferred labels are typically characterized by one or more of the following: high sensitivity, high stability, low background, low environmental sensitivity and high specificity in labeling. Fluorescent moieties, which are incorporated into the labels of the invention, are generally are known, including Texas red, digoxigenin, biotin, 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes, flavin and many others. Many fluorescent tags are commercially available from the SIGMA chemical company (Saint Louis, Mo.), Molecular Probes, R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka ChemicaBiochemika Analytika (Fluka Chemie AG, Buchs, Switzerland), and Applied Biosystems (Foster City, Calif.), as well as many other commercial sources known to one of skill.

The labels are covalently bound to the novel cholesterol inhibitors of the invention by a tether group. The tether group can be any moiety capable of covalently linking to the inhibitors and to the labels. Preferred groups are substituted or unsusbstituted alkylene, alkenylene or alkynylene of 1 to 10 carbon atoms, more preferably 1 to 4 carbon atoms. Particularly preferred groups are unsusbstituted alkynylenes.

The candidate and actual inhibitory agents of this invention will preferably take the form of organic compounds, particularly compounds which inhibit the absorption of cholesterol mediated by SR-BI and other proteins3. Other inhibitory agents may be proteins, particularly antibodies and antibody derivatives. Recombinant expression systems may be used to generate quantities of SR-BI sufficient for production of monoclonal antibodies (MAbs) specific for SR-BI. Suitable antibodies for cholesterol absorption inhibition will bind to SR-BI in a manner reducing or eliminating the cholesterol binding activity, typically by obscuring the binding site. Suitable MAbs may be used to generate derivatives, such as Fab fragments, chimeric antibodies, altered antibodies, univalent antibodies, and single domain antibodies, using methods known in the art.

EXAMPLES

Example 1

A. PREPARATION OF 6-(6-HYDROXY-3-OXO-3H-XANTHEN-9-YL)-N-(5-PROP-2-YNYLCARBAMOYL-PENTYL)-ISOPHTHALAMIC ACID (1)

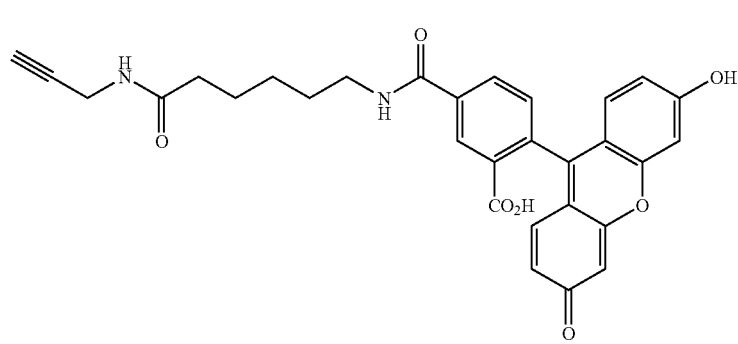

Added propargyl amine (5 μL, ~4 mg, 73 μmol) to 0.3 mL DMF containing 3-5 drops 0.2M aqueous NaHCO₃ then added 6-(Fluorescein-5-carboxamido)hexanoic acid, succinimidyl ester (5-SFX; Molecular Probes, Inc.) (5 mg, 8.5 μmol) to the mixture. Stirred the bright orange solution for 3 h at room temperature. Concentrated in vacuo and chromatographed the residue over ~5 g of silica gel eluting with 10% MeOH in dichloromethane to give the desired terminal alkyne (1) as a yellow brown fluorescent oil. calcd m/z for $C_{30}H_{27}N_2O_7$=527; found m/z=527.

B. PREPARATION OF 1-O-[4-[TRANS-(3R,4S)-1-[4-[3-[[6-[[[3-CARBOXY-4-(6-HYDROXY-3-OXO-3H-XANTHEN-9-YL)PHENYL]CARBONYL]AMINO]-1-OXOHEXYL]AMINO]-1-PROPENYL]PHENYL]-3-[3-(S)-HYDROXY-3-(4-FLUOROPHENYL)PROPYL]-2-OXO4-AZETIDINYL]PHENYL]-BETA-D-GLUCORONIC ACID (IB)

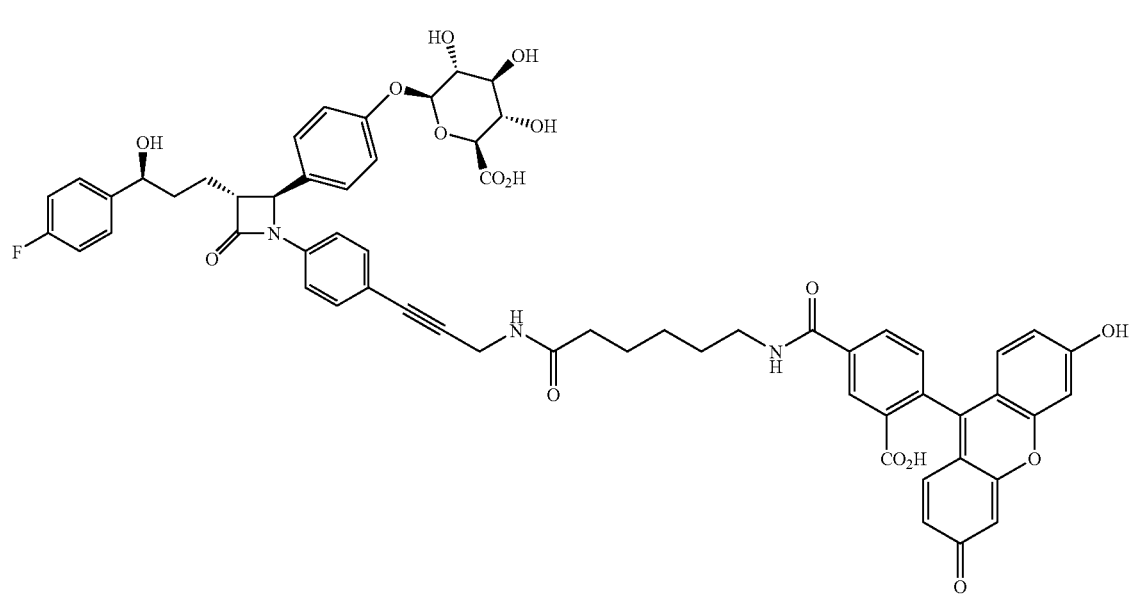

To the iodophenylazetidinone glucuronide methyl ester IIIA (disclosed in Pat. No. 5,756,470, May 26, 1998) (6.7 mg, 9.47 μmol) in 0.8 mL DMF, was added the alkyne (1) (14.8 mg, 28 μmol). Bubbled argon through the reaction mixture, then added palladium tetrakistriphenylphosphine (1.4 mg, 1.2 μmol), copper(I) iodide (0.8 mg, 4.2 μmol), and triethylamine (8 μL, 57 μmol). Stirred the reaction mixture overnight under argon. Concentrated the reaction onto a prep TLC plate and eluted with 25% MeOH in dichloromethane. Collected the major fluorescent band and purified further by reverse phase HPLC over a C-18 column eluting with 10-100% acetonitrile in water affording the desired fluorescent methyl ester as an orange solid. FABMS: calcd m/z for $C_{61}H_{57}N_3FO_{16}$ $(M+1)^+$ 1106.4; found m/z=1106.5.

The glucuronide methyl ester was then hydrolyzed by dissolving 9 mg of the compound in 2 mL of a 7:2:1 mixture of water:triethylamine: methanol and stirring for 1 h. Evaporation to dryness gave the desired fluorescent azetidinone glucuronide, (IB) as an orange solid. ES-MS: calcd m/z for $C_{60}H_{55}N_3FO_{16}$ $(M+1)^+$=1092.3; found m/z=-1092.3.

Example 2

A. PREPARATION OF 4,4-DIFLUORO-5,7-DIMETHYL4-BORA-3a,4a-DIAZA-s-INDACENE-3-N-PROP-2-YNYL-PROPIONAMIDE (2)

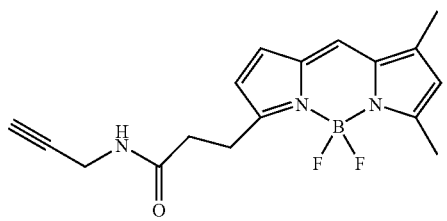

To propargyl amine (8 μL, ~6.4 mg, ~117 μmol) in 0.5 mL DMF and 1 drop of 0.1M NaHCO3, was added 4,4-difluoro-5,7-dimethyl4-bora-3a,4a-diaza-s-indacene-3-propionic acid, succinimide ester (BODIPY FL, SE; Molecular Probes, In.) (10 mg, 25.7 μmol) in 0.1 mL DMF. Stirred the reaction at room temperature for 12 h. Concentrated the mixture in vacuo and chromatographed the residue over ~5 g silica gel eluting with 1% MeOH in dichloromethane to give the desired alkyne (2) as a yellow orange oil. $R_f$=0.62 in 5% MeOH in $CH_2Cl_2$ on $SiO_2$ TLC.

B. PREPARATION OF [1-O-[4-[1-[4-[3-[[3-[2-[(3, 5-DIMETHYL-1H-PYRROL-2-YL-.KAPPA.N) METHYLENE]-2H-PYRROL-5-YL-.KAPPA.N]-1-OXOPROPYL]AMINO]-1-PROPYNYL]PHENYL]- 3(R)-[3(S)-HYDROXY-3-(4-FLUOROPHENYL) PROPYL]-2-OXO-4(S)-AZETIDINYL]PHENYL]- BETA-D-GLUCURONATO]DIFLUOROBORATE, HYDROGEN (IC)

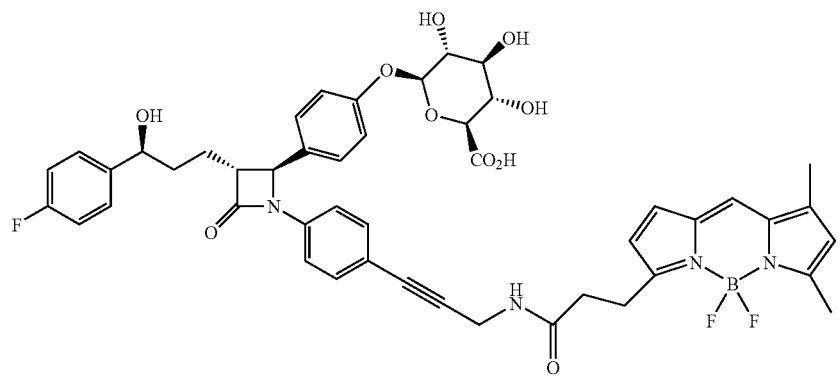

To the iodophenylazetidinone glucuronide methyl ester IIIA (disclosed in Pat. No. 5756,470 May 26, 1998) (7.7 mg, 10.9 μmol) in 1 mL DMF, was added (7.2 mg, 10.9 μmol) of the BODIPY alkyne (2). Bubbled argon through the solution for a few minutes and then added palladium tetrakistriphenylphosphine (1.2 mg, 1 μmol), copper(I) iodide (0.6 mg, 3 μmol), and triethylamine (10 μL, 7 μmol). Stirred the reaction overnight under argon. Removed the solvent in vacuo and purified the product via prep TLC eluting with a 50:50:17:1 mixture of ethyl acetate:hexanes:methanol:acetic acid to give the desired fluorescent methyl ester as an orange solid. ESI-MS: calcd m/z for $C_{48}H_{49}BF_3N_4O_{10}$ $(M+1)^+$=909.3; found m/z=909.2.

The glucuronide methyl ester was then hydrolyzed by dissolving 4.2 mg of the compound in ~1 mL of a 7:2:1 mixture of water:triethylamine: methanol and stirring for 1 h. Evaporation to dryness gave the desired fluorescent azetidinone glucuronide (IC) as an orange solid, ES-MS: calcd m/z for $C_{47}H_{46}BF_2N_4O_{10}$ $(M+1-HF)^+$=875.3; found m/z=875.3.

Example 3

DETERMINATION OF CHOLESTEROL ABSORPTION INHIBITORY ACTIVITY

Male Sprague-Dawley rats weighing 300-400 g were used. After an overnight fast, rats were anesthetized (Inactin, 0.1 mg/kg i.p.) for the duration of each study and were fitted with a cannula into the small intestine just below the pyloric valve. For the cannulation of the small intestine, a catheter (Surflo® i.v. catheter (18GX2"), Terumo Medical Corporation; Elkton, Md.) was inserted through the fundus of the stomach, advanced 1 cm beyond the pylorus, and ligated in place. Compounds were mixed in rat bile and delivered by bolus injection (1 mL) via the intestinal catheter into the small intestine.

One hour after the bile doses were delivered, three mL of an emulsion consisting of 2.23 mg/mL L-phosphatidylcholine and 11.8 mg/mL triolein in 19 mM sodium taurocholate (Sigma; St. Louis, Mo.) buffer (pH 6.4) containing 3 mg cholesterol and 1 mCi $^{14}$C-cholesterol (NEN; Boston, Mass.) was delivered to each rat as a bolus via the intestinal cannula. Ninety minutes after the cholesterol emulsion was delivered, the rats were euthanized. Blood was collected and plasma was separated by centrifugation at 2000 rpm for 15 min at 4° C. Triplicate aliquots of plasma were analyzed $^{14}$C radioactivity and inhibition of cholesterol absorption relative to bile vehicle control rats was determined.

The ID50 for IIA in this acute model of cholesterol absorption was calculated to be 0.0015 mg/kg (Van Heek, M., France, C. F., Compton, D. S., McLeod, R. L., Yumibe, N. P., Alton, K. B., Sybertz, E. J., and Davis, H. R.: In vivo mechanism-based discovery of a potent cholesterol absorption inhibitor (IIA) through the identification of the active metabolites of IVA. The Journal of Pharmacology and Experimental Therapeutics (JPET), 283: 157-163, 1997).

TABLE 1

In Vivo Cholesterol Absorption Activity:

| Compound # | Dose (μg/kg) | % Inhibition of [14C]-Cholesterol Absorption into Plasma |
|---|---|---|
| IA | 10 | 91% |
| IB | 56 | 79% |
| IB | 186 | 88% |
| 1C | 30 | 58% |
| 1C | 100 | 80% |

IA is the glucuronide of IIA

Example 4

IDENTIFICATION OF PROTEINS INVOLVED IN CHOLESTEROL ABSORPTION AND TRAFFICKING; EXPRESSION CLONING EXPERIMENTS

The small intestine was removed from male CRL: CD BR rats. Intestinal epithelial cells were isolated by the method of Weiser (Weiser, M., 1973, JBC 248, 2536-2541) and the mRNA extracted. Poly A mRNA was purified and double stranded cDNA synthesized. Adapter linkers were ligated followed by size selection (>2 Kb) of the cDNA. The selected fraction of cDNA was ligated into the retroviral expression plasmid pMX, subsequently transformed into bacteria and grown on selective agar at a clonal density of ~30,000/plate. Each pool of bacterial clones was collected and plasmid DNA prepared.

Individual pools of cDNA library were transformed into the retroviral packaging cell line BOSC23 and the resulting viral particles, containing the cDNA library, were used to infect the mouse cell line BW5147. Following infection BW5147 cells were stained with compound 1C and analyzed by fluorescent activated cell sorting (FACS). Positive staining cells (~01%) were recovered and re-cultured. The process of recovering positive staining cells was repeated after expansion of the cell population in culture and following the second round of FACS analysis individual cells were isolated by limiting dilution.

Individual clonal populations of cells were subjected to PCR using retroviral vector specific oligonucleotide primers designed to flank the multiple cloning site in which the cDNA library was cloned. Resulting DNA fragments were subcloned and completely sequenced to determine the identification of the cloned cDNA. By sequencing two clones isolated from two independent cDNA expression libraries, Scavenger receptor, class B, type I (SR-BI) (GENBANK Accession Numbers: U76205 —submission date Oct. 24, 1996; D89655—submission date Dec. 3, 1996, and AB002151—submission date Mar. 26, 1997) was identified as the cellular receptor for compound IC.

The above described method may be used in conjunction with any of the azetidinone compounds referred to herein to identify other proteins that are involved in cholesterol absorption or trafficking.

Once identified, further characterization of the proteins can be conducted, for example, using the following methods:

(1) FACS analysis of target expressing cells with fluorescent compound binding can be utilized in both direct and competition binding formats. Added complexity by the addition of other cellularly expressed proteins as well as the addition of exogenous molecules such as antibodies and other soluble factors can also be examined; and (2) Equilibrium and competition binding can be conducted in similar fashion to radiolabeled ligand analysis by simply substituting a fluorescent spectrophotometer for a scintillation counter and measuring cell associated fluorescence instead of radioactivity.

What is claimed is:

1. An isolated cell wherein a fluorescent cholesterol absorption inhibitor is bound to a surface of said cell, wherein said inhibitor is an azetidinone.

2. The cell of claim 1 wherein said inhibitor is represented by structural formula I or II:

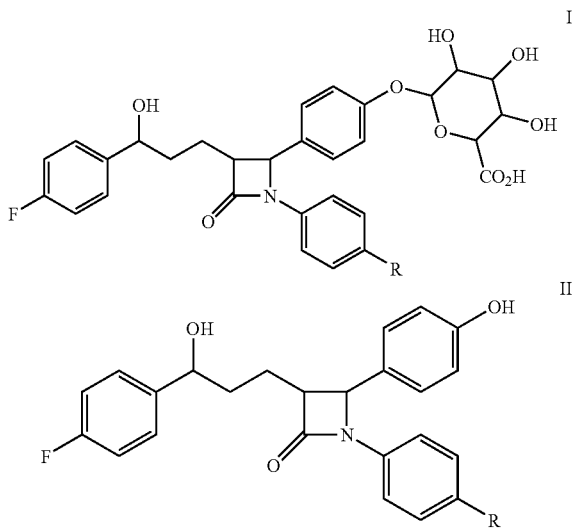

wherein R is a fluorescent moiety.

3. The cell of claim 2 wherein R is linked to the fluorescent moiety by an alkynyl containing tethering group.

4. The cell of claim 3 wherein R is represented by a structural formula selected from the group consisting of:

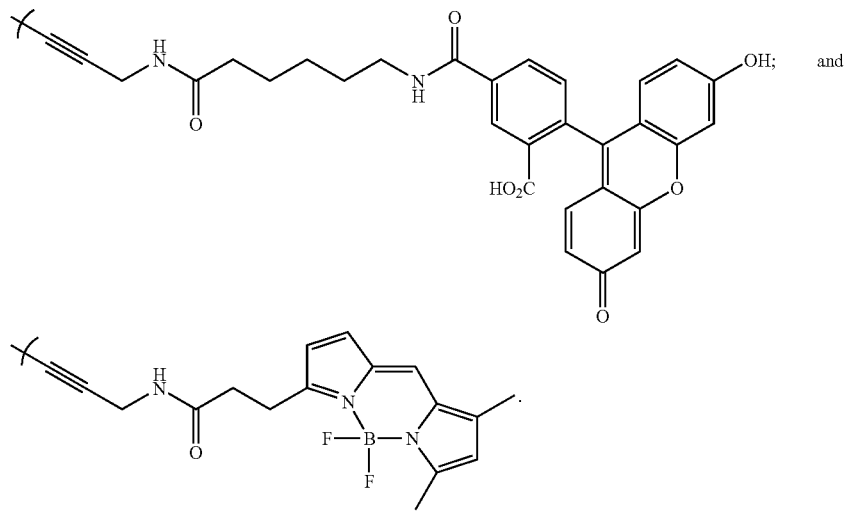
5. The cell of claim 1 which comprises a cDNA that is a member of a cDNA library.
6. The cell of claim 1 which is a BW5147 cell.
* * * * *